(12) United States Patent
Kordonski et al.

(10) Patent No.: US 7,888,929 B2
(45) Date of Patent: Feb. 15, 2011

(54) METHOD AND APPARATUS FOR MEASUREMENT OF MAGNETIC PERMEABILITY OF A MATERIAL

(75) Inventors: William Kordonski, Webster, NY (US); Arpad Sekeres, Rochester, NY (US); Robert James, Rochester, NY (US)

(73) Assignee: Cabot Microelectronics Corporation, Aurora, IL (US)

( * ) Notice: Subject to any disclaimer, the term of this patent is extended or adjusted under 35 U.S.C. 154(b) by 24 days.

(21) Appl. No.: 12/449,655

(22) PCT Filed: Feb. 27, 2008

(86) PCT No.: PCT/US2008/055053

§ 371 (c)(1),
(2), (4) Date: Aug. 19, 2009

(87) PCT Pub. No.: WO2008/109301

PCT Pub. Date: Sep. 12, 2008

(65) Prior Publication Data
US 2010/0079137 A1   Apr. 1, 2010

Related U.S. Application Data

(63) Continuation-in-part of application No. 11/681,258, filed on Mar. 2, 2007, now Pat. No. 7,557,566.

(51) Int. Cl.
*G01N 27/74*   (2006.01)
*G01B 7/00*   (2006.01)
*B24B 1/00*   (2006.01)

(52) U.S. Cl. .......................... 324/204; 324/239; 451/36
(58) Field of Classification Search ................. 324/204, 324/207.15–207.19, 228, 232, 234, 239–240; 188/267, 267.2; 210/222; 451/8, 36
See application file for complete search history.

(56) References Cited

U.S. PATENT DOCUMENTS

| | | | | |
|---|---|---|---|---|
| 2,790,950 A | * | 4/1957 | Miller | ........................ 324/227 |
| RE34,039 E | * | 8/1992 | Kobayashi et al. | ..... 73/862.336 |
| 2003/0020463 A1 | * | 1/2003 | Carlson et al. | .............. 324/204 |

* cited by examiner

*Primary Examiner*—Bot L LeDynh
(74) *Attorney, Agent, or Firm*—Thomas E. Omholt; Steven D. Weseman

(57) ABSTRACT

A system for determining magnetic permeability of a material. Two electrical inductors formed as primary and secondary concentric coils share a common magnetic core space. A first AC voltage applied to the primary coil creates a magnetic flux in the core proportional to the magnetic permeability of the material. The magnetic flux induces an AC voltage in the secondary coil indicative of the apparent magnetic permeability of the sample. The apparent permeability is corrected for conductivity by imposing a second AC voltage and resistor in series across first and second electrodes disposed in the material. When the material is a magnetorheological fluid, the magnetic permeability is proportional to the concentration of magnetic particles in the sample and can be back-calculated from the amplitude of the secondary voltage signal.

8 Claims, 2 Drawing Sheets

METHOD AND APPARATUS FOR MEASUREMENT OF MAGNETIC PERMEABILITY OF A MATERIAL

RELATIONSHIP TO OTHER APPLICATIONS AND PATENTS

The present application is a Continuation-In-Part of a U.S. patent application Ser. No. 11/681,258, filed Mar. 2, 2007 now U.S. Pat. No. 7,557,566.

BACKGROUND OF THE INVENTION

1. Field of The Invention

The present invention relates to methods and apparatus for inferential measurement; more particularly, to methods and apparatus for determining the magnetic permeability of a material; and most particularly, to a method and apparatus for using such measurement to control the concentration of a magnetic material in a magnetorheological (MR) fluid.

2. Discussion of the Related Art

MR fluids are well known and may be defined practically as fluid materials whose apparent viscosities are reversibly increased by exposure of the fluid to a magnetic field. The increase in viscosity is anisotropic, being greatest in the direction of the magnetic field due to formation of fibrils of magnetized particles. This property, known in the art as "stiffenening", has been employed to great success in the field of extremely high resolution shaping, finishing, and polishing of surfaces, especially optical elements, wherein very small amounts of material may be removed in a highly precise and controlled manner. This field is known generally in the art as magnetorheological finishing (MRF). See, for example, U.S. Pat. Nos. 5,971,835; 6,746,310; and 6,893,322, the relevant disclosures of which are incorporated herein by reference.

A problem in the art of MRF is maintaining a constant magnetic particle concentration in the MR fluid entering the magnetic work zone. MR fluid is supplied to the work zone by a delivery system that draws MR fluid from a mixing sump into which used MR fluid passes from the work zone for mixing and reuse. The used MR fluid typically is depleted in carrier (water) by evaporation and also is heated, both of which alterations must be corrected before the MR fluid may be reused. Without replenishment of water lost to evaporation, the bulk supply of MR fluid in the sump will gradually increase in particle concentration during an MRF operation. This is an undesirable operating condition because particle concentration is an important factor governing the rate of removal of material from a substrate being finished. Thus, it is important to know what the particle concentration is in the MR fluid being supplied from the sump at any given time and to provide a proper water replenishment rate to the sump to replace the water lost to evaporation in use, thereby dynamically keeping the concentration constant at an aim value.

U.S. Pat. No. 5,554,932 discloses a system for measuring magnetic saturation flux density of a sample material. First and second sample holders are disposed symmetrically on either side of a cylindrical permanent magnet. Coils are placed around the sample holders and the permanent magnet is rotated. The signals induced in the coils in the absence of a magnetic material in one of the sample holders are applied to an amplifier/meter in such a manner as to provide a null signal. When a sample is placed in one of the sample holders, the magnetic saturation flux density can be measured. A shortcoming of the disclosed system is that the mechanical device is relatively cumbersome and has a critical moving part (the permanent magnet).

U.S. Pat. No. 6,650,108 discloses a system for inferring concentration of magnetic particles in a flowing MR fluid. The system is based on inductance measurement that converges in an impedance measurement with relatively complex technique involving high sensitivity electric bridge circuits. A shortcoming of the disclosed system is that resolution is relatively low.

U.S. patent application Ser. No. 11/681,258, filed Mar. 2, 2007, discloses a simple, high-resolution means for continuously measuring and monitoring the concentration of magnetic particles in the mixed sump MR fluid to permit controlled real-time dilution thereof before the sump MR fluid is reused for finishing. A shortcoming of the disclosed system is that the apparent concentration (magnetic permeability) is also a function of the electrical conductivity of the MR fluid.

What is needed in the art is a simple, high-resolution means for continuous compensation of output signal for changes in fluid conductivity in the mixed sump MR fluid to permit controlled real-time dilution thereof before the sump MR fluid is reused for finishing.

It is a principal object of the present invention to include consideration of fluid conductivity in determining, particle concentration in an MR fluid.

SUMMARY OF THE INVENTION

Briefly described, in a method and apparatus of the present invention, two electrical inductors share the same magnetic core. Preferably, the inductors are formed as primary and secondary concentric coils. When an AC voltage is applied to the primary coil, an axially-directed magnetic flux is created in the core which is proportional in intensity to the magnetic permeability of the core. In turn, due to the effect of mutual inductance, the magnetic flux induces an AC voltage in the secondary coil which is in phase with the source voltage. The magnetic permeability of the core depends upon the concentration of magnetic particles in the sample (when the "core" is a sample of MR fluid), and thus the concentration of magnetic particles can be back-calculated from the amplitude of the secondary voltage signal.

Sensitivity of measurements and system resolution can be increased by using a differential approach using two identical sets or pairs of coils wherein a reference material forms a magnetic core for one coil set and the MR fluid forms a magnetic core for the other coil set.

Because magnetically-induced circulating eddy currents in the liquid conductive core generate magnetic field that is opposite to the external magnetic field, the apparatus output signal may be affected. The strength of such eddy currents is a function of conductivity of the MR fluid, which can change over time due to chemical processes such as oxidation occurring during the working life of the MR fluid. Therefore a conductivity term must be included when calculating the voltage output of the apparatus, and conductivity of the MR fluid must be measured continuously during use.

BRIEF DESCRIPTION OF THE DRAWINGS

The foregoing and other objects, features, and advantages of the invention, as well as presently preferred embodiments thereof, will become more apparent from a reading of the following description in connection with the accompanying drawings in which.

DETAILED DESCRIPTION OF THE INVENTION

Figure 1:
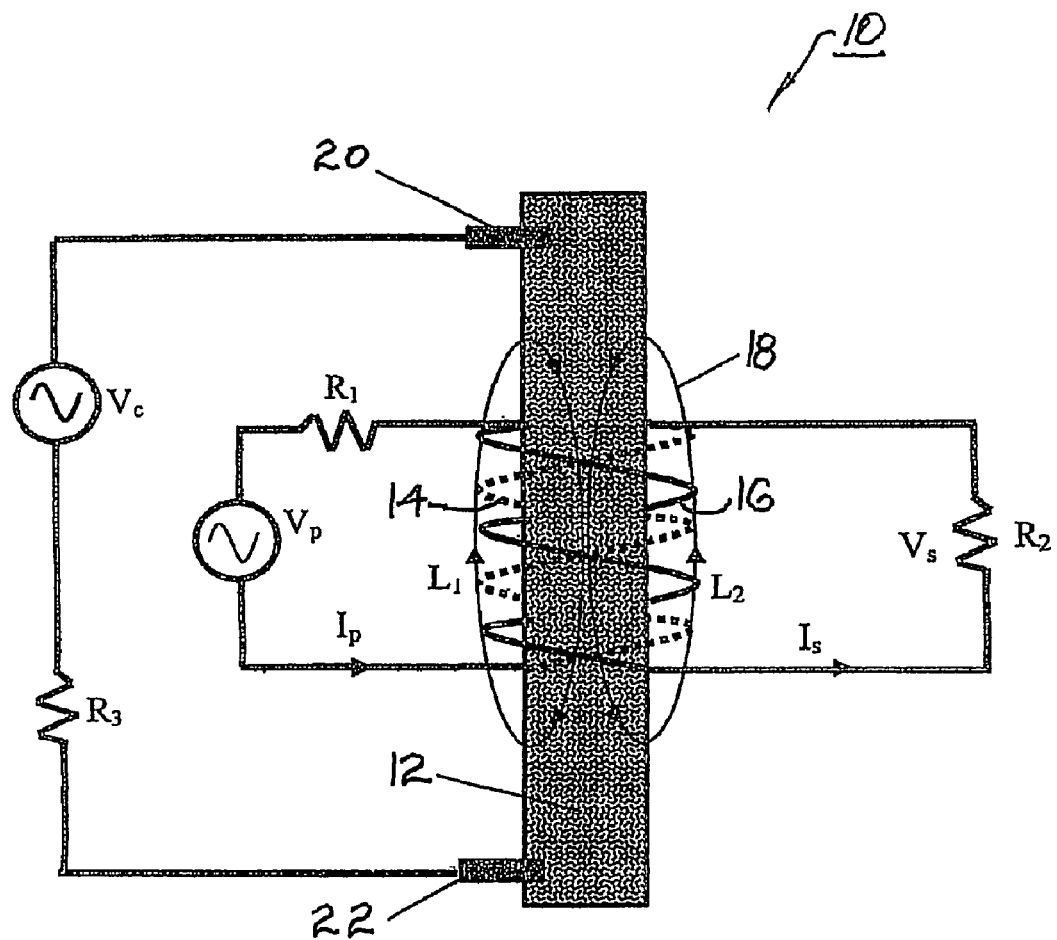
FIG. 1 is a schematic drawing of an exemplary embodiment of a system in accordance with the invention for measuring magnetic permeability, including means for continuously measuring conductivity.

Referring to FIG. 1, in a system 10 in accordance with the invention suitable for measuring the magnetic permeability of the material of a magnetic core 12, two inductors (primary coil 14 and secondary coil 16) share magnetic core 12, which is a sample of a magnetic material to be tested, such as an MR fluid in the sump of an MR finishing machine. When an AC voltage $V_p$ is applied to primary coil 14, an axially-directed magnetic flux 18 is created in core 12 in accordance with Equation 1:

$$B = \mu \frac{N}{l} \frac{I_p}{\sqrt{2}} \quad \text{(Eq. 1)}$$

where μ is the magnetic permeability of the core, N is the number of primary coil turns, l is the coil's length, $I_p$ is the current amplitude, and $I_p/\sqrt{2}$ is the root mean square current.

In turn, due to the effect of mutual inductance, magnetic flux 18 induces an AC voltage $V_s$ in secondary coil 16 in phase with the source voltage in accordance with Equation 2:

$$V_s = 2\pi f N A B \quad \text{(Eq. 2)}$$

where f is current frequency and A is the cross-sectional area of core 12. From Equation 1 and Equation 2, it follows that the root mean square voltage $V_s$ generated in secondary coil 16 is given by Equation 3:

$$V_S = 4.44 \, \mu f \, \frac{N^2 A}{l} I_p \quad \text{(Eq. 3)}$$

Primary coil 14 behaves as a load with respect to the AC voltage source $V_p$, and secondary coil 16 behaves as a source with respect to resistor $R_2$. At the same time, the magnetic permeability μ depends on magnetic properties of core 12. In turn, these properties are dependent on concentration φ of the magnetic particles in the sample, as given by Equation 4:

$$\mu = f(\phi) \quad \text{(Eq. 4)}$$

Figure 2:
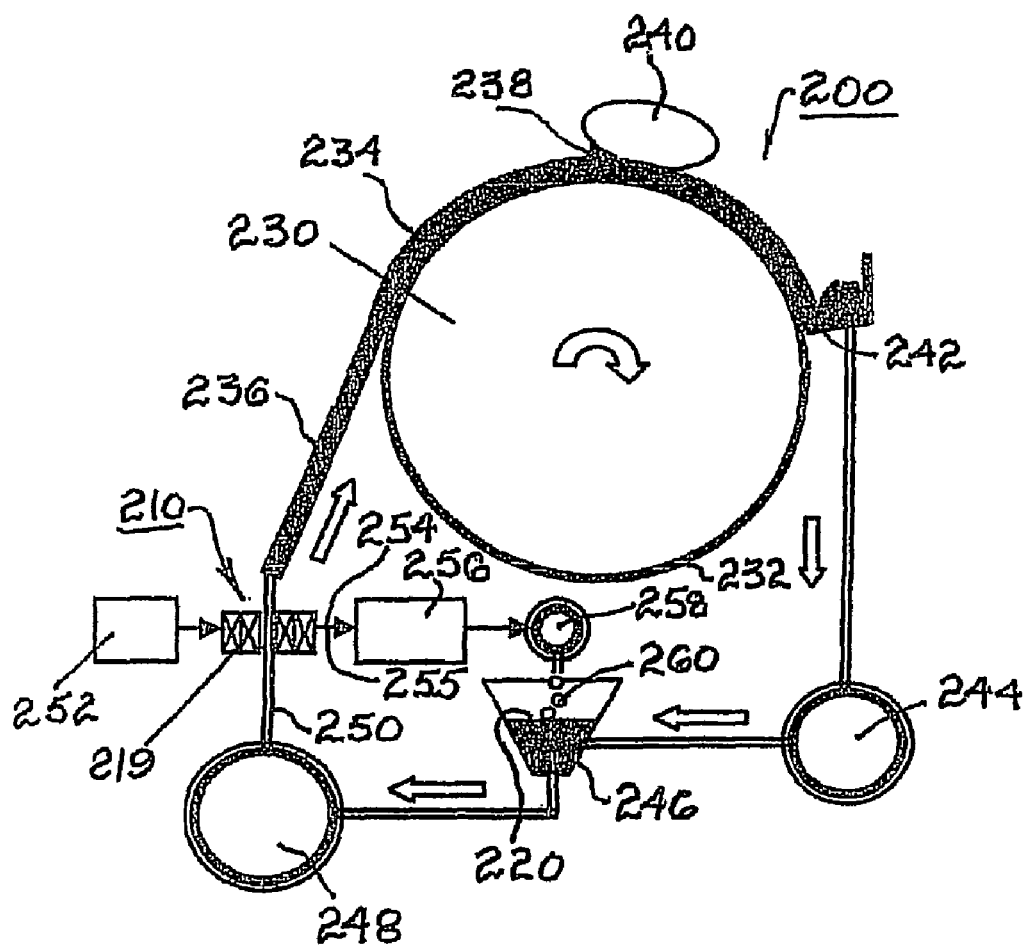
FIG. 2 is a schematic drawing showing application of the exemplary embodiment in an MR fluid finishing machine.

When all parameters of system 10, including the AC voltage applied to the primary coil, are held constant, any variation in concentration of magnetic particles concentration in magnetic core 12 will result, as it follows from Equation 3, in the proportional change of AC voltage $V_s$ in secondary coil 16. In doing so, the system output signal follows variations in the sample magnetic particles concentration. In the general case, it can be defined as shown in Equation 5:

$$V_s = f(\phi, k_1, k_2 \ldots) \quad \text{(Eq. 5)}$$

where $k_1, k_2 \ldots$ are some constant parameters which depend on system geometry and system electrical parameters. The magnitude of output signal can be manipulated by (pre)setting different system parameters such as number of turns and geometries of the coils, frequency and voltage of the oscillator, impedance of the components, and the like. System 10 further may contain a temperature sensor (not shown), such as a thermistor, means to compensate for thermal variation in circuit impedance and change in output signal due to variations of temperature, and an electronic controller for processing data from system 10, calculating the magnetic permeability, and controlling replenishment of the MR fluid in the sump as shown in FIG. 2 and described below.

At the same time, MR fluid is a water-based suspension of micron-size iron and abrasive particles. To retard particles sedimentation and corrosion, the fluid contains some chemical additives which result in relatively high fluid pH and conductivity. When such conductive fluid is placed in an AC magnetic field, eddy-currents are induced within the conductive material in closed circular paths which are perpendicular to the inducing external magnetic field. Such induced eddy-currents oppose changes in the inducing external magnetic field and as a result, an AC magnetic field produced by the circulating eddy-currents may reduce the larger external AC magnetic field and therefore reduce the apparatus output signal.

Further, fluid conductivity may vary in time due to chemical processes (oxidation) occurring during fluid life in an MRF machine, resulting in instability of the output signal and consequent errors in fluid monitoring and material removal rate.

What is more, an additional source of error is dependence of fluid conductivity on concentration of iron particles, which is the primary function to be measured by the present method.

What is needed is a simple, high-resolution means for continuous compensation of output signal for changes in fluid conductivity in the mixed sump MR fluid to permit controlled real-time dilution thereof before the sump MR fluid is reused for finishing.

For this purpose, the fluid conductivity is continuously measured. System 10 includes two electrodes 20,22 disposed in the MR fluid core 12 at opposite ends of primary and secondary coils 14,16 and connected to a voltage source $V_c$ (AC, 10,000 Hz to avoid polarization of electrodes) through resistor $R_3$. A voltage from resistor $R_3$ is proportional to conductivity of MR fluid core 12, and may be used in the controller to compute and compensate for conductivity variation in circuit impedance and change in output signal due to variations of conductivity.

In this case, a conductivity-adjusted output signal $V_{s1}$ can be defined as a variation on Equation 5 wherein a conductivity term is added:

$$V_{s1} = f(\phi, k_1, k_2 \ldots) + \psi(G) \quad \text{(Eq. 6)}$$

where G is fluid conductivity

A proper quantitative relationship between the concentration and the voltage $V_{s1}$ in the secondary coil is determined by calibration with samples of known magnetic particles concentration, which calibration gives the following general expression for concentration:

$$\phi = a V_{s1} + b \quad \text{(Eq. 7)}$$

where a and b are constants defined by calibration.

Referring to FIG. 2, an exemplary application is shown for a system 210 in accordance with the present invention in assisting in maintaining a constant concentration of magnetic particles in MR fluid in an MR finishing apparatus 200.

As is known in the prior art for an MR finishing apparatus 200 and described more fully in the incorporated references, a carrier wheel 230 has a surface 232, preferably spherical, for receiving a ribbon 234 of MR fluid in a non-stiffened state from nozzle 236. Surface 232 carries ribbon 234 into a work zone 238 between surface 232 and an off-spaced work piece 240 to be finished. Shaped magnetic pole pieces (not shown) create an oriented magnetic field within work zone 238 that causes the MR fluid therein to become stiffened to a consistency approximating putty. The stiffened MR fluid, which may also contain non-magnetic particles of abrasives such as cerium oxide, ablates the surface of work piece 240 in controlled fashion as it is drawn through work zone 238. Carrier surface 232 continuously supplies and removes MR fluid to and from work zone 238. A scraper 242 removes used MR fluid, no longer stiffened, from carrier surface 232 and returns it via a suction pump 244 to a mixing sump 246, wherein the used MR fluid is mixed with a bulk supply of MR fluid 220 and from whence mixed MR fluid 220 is drawn by delivery pump 248 and supplied again to nozzle 236 via non-magnetic tube 250.

A mutual inductance sensor 219 supplied with means for MR fluid conductivity measurements in accordance with the present invention and controllably driven by an AC power supply 252 as described above is placed concentrically outside non-magnetic tube 250 filled with flowing MR fluid 220. Output signals 254 and 255 from sensor 219 are directed to a programmable controller 256, programmed with algorithms and look-up tables in accordance with Equations 1 through 7 and having a set point corresponding to an aim concentration, which controls a pump 258 to dispense replenishment water 260 into sump 246 at a controlled flow rate to compensate for water evaporated from the MR fluid ribbon 234 when exposed on carrier wheel 230 during use thereof. Replenishment water 260 is mixed with the bulk supply MR fluid within sump 246 to dilute the bulk concentration to aim. Thus, the concentration of magnetic particles in MR fluid 220 as drawn from sump 246 for supply to work zone 238 is maintained at the aim concentration, providing a stable and predictable rate of material removal from work piece 240.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

What is claimed is:

1. A system for determining magnetic permeability of a material, comprising:
    a) a first electrical inductor;
    b) a second electrical inductor;
    c) a first AC voltage source connected to said first electrical inductor to induce a magnetic field surrounding said first and second electrical inductors and a sample of said material;
    d) apparatus for measuring an induced AC voltage signal in said second electrical inductor; and
    e) first and second electrodes immersed in said sample of said material and connected in series with a variable AC voltage source and a resistor for determining a voltage signal proportional to the conductivity of said sample of material, which signal is added to said induced AC voltage signal from said second electrical inductor to provide a conductivity-corrected induced AC voltage signal indicative of magnetic permeability of said sample.

2. A system in accordance with claim 1 wherein said first electrical inductor is a first coil, said second electrical conductor is a second coil coaxial with said first coil, said magnetic field is axially-directed within said first and second coils, and said sample of said material is disposed within said axially-directed magnetic field.

3. A system in accordance with claim 2 wherein said second coil is wrapped around said first coil.

4. A system in accordance with claim 1 wherein said material is a magnetorheological fluid comprising magnetic particles dispersed in a liquid carrier and wherein said magnetic permeability is proportional to the concentration of magnetic particles in said liquid carrier.

5. A system in accordance with claim 2 wherein said system is a component of a magnetorheological finishing system.

6. A method for determining magnetic permeability of a material, comprising the steps of:
    a) providing a first electrical inductor;
    b) providing a second electrical inductor;
    c) providing an AC voltage source connected to said first electrical inductor to induce a magnetic field surrounding said first and second electrical inductors;
    d) providing apparatus for measuring an induced AC voltage in said second electrical inductor;
    e) providing apparatus for measuring conductivity of said material;
    f) positioning a sample of said material within said magnetic field; and
    g) determining an amplitude of said induced AC voltage corrected for conductivity of said material, wherein a conductivity-corrected amplitude of said induced AC voltage is proportional to said magnetic permeability of said material.

7. A method in accordance with claim 6 wherein said first electrical inductor is a first coil, said second electrical conductor is a second coil coaxial with said first coil, said magnetic field is axially-directed within said first and second coils, and said sample of said material is disposed within said axially-directed magnetic field.

8. A magnetorheological finishing system comprising:
    a) a sump for storage of a bulk supply of magnetorheological fluid to supply and receive magnetorheological fluid during recirculating use thereof in said system, wherein said magnetorheological fluid comprises magnetic particles dispersed in a carrier fluid, and wherein the concentration of said particles in said carrier fluid is increased during said recirculating use by evaporative loss of a portion of said carrier fluid;
    b) a double-coil mutual inductance sensor including a primary coil and a secondary coil coaxially wound, defining a sample space within said primary and secondary coils for receiving a sample of said magnetorheological fluid from said bulk supply;
    c) means for imposing an AC voltage on said primary coil;
    d) means for sending a first signal from said secondary coil representing amplitude of an AC voltage induced therein, said signal being proportional to the concentration of said magnetic particles in said carrier fluid in said sample;
    e) means for determining conductivity of said magnetorheological fluid and for sending a second signal indicative of said conductivity;
    f) controller means responsive to said first and second signals and having programmed means for processing said first and second signals and comparing a resulting signal to a stored reference signal indicative of an aim concentration of said magnetic particles dispersed in said carrier fluid and for calculating a flow rate of replenishment carrier fluid required for addition to said sump to replace said evaporative loss and thereby maintain said bulk supply of said magnetorheological fluid at said aim concentration; and
    g) dispensing means responsive to said controller means for dispensing said replenishment carrier fluid into said bulk supply at said calculated flow rate.

* * * * *